US00PP35567P2

(12) United States Plant Patent
Podaras

(10) Patent No.: US PP35,567 P2
(45) Date of Patent: Jan. 2, 2024

(54) ***BUDDLEIA* PLANT NAMED 'PODARASNGA 3-30'**

(50) Latin Name: ***Buddleia* x *hybrida* (*Buddleia davidii* x *B. crispa* x *B. alternafolia* x *B. lindleyana*)**
Varietal Denomination: PODARASNGA 3-30

(71) Applicant: Early Morning LLC, Greendale, IN (US)

(72) Inventor: Peter Podaras, Boring, OR (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 17/978,395

(22) Filed: Nov. 1, 2022

(51) Int. Cl.
*A01H 5/00* (2018.01)
*A01H 6/00* (2018.01)

(52) U.S. Cl.
USPC ..... Plt./242

(58) Field of Classification Search
USPC ..... Plt./242
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Buddleia* plant particularly distinguished by extremely dense growth, very dense branching, an extremely high number of flower panicles and a very fastigiate habit, is disclosed.

1 Drawing Sheet

Genus and species: *Buddleia* x *hybrida* (*Buddleia davidii* x *B. crispa* x *B. alternafolia* x *B. lindleyana*).
Variety denomination: 'PODARASNGA 3-30'.

BACKGROUND OF THE NEW PLANT

The present invention relates to a new and distinct variety of *Buddleia* hereinafter referred to by the variety name 'PODARASNGA 3-30'.

'PODARASNGA 3-30' arose from a deliberate cross between two un-named, proprietary and unpatented *Buddleia* seedlings in Salem, Oregon. Seeds from the cross were sown in April 2014 in Salem Oregon and further grown in Tipp City, Ohio. 'PODARASNGA 3-30' was selected in July 2017 in Tipp City, Ohio from the seedling population.

'PODARASNGA 3-30' was first asexually propagated in August 2017 in Tipp City, Ohio by softwood cuttings. 'PODARASNGA 3-30' was found to reproduce true to type in successive generations of asexual propagation via softwood cuttings.

SUMMARY

The following are the most outstanding and distinguishing characteristics of this new variety when grown under normal horticultural practices in Boring, Oregon and Tipp City, Ohio and Boring, Oregon.

1. Extremely dense growth;
2. Very dense branching;
3. Extremely high number of flower panicles; and
4. Very fastigiate habit.

DESCRIPTION OF THE PHOTOGRAPHS

This new *Buddleia* plant is illustrated by the accompanying photograph which shows the plant's overall plant habit including form, inflorescence, and foliage. The photograph is of a 5-month-old plant taken in September 2022 and grown outdoors in Boring, Oregon. The colors shown are as true as can be reasonably obtained by conventional photographic procedures. The Figure shows the overall plant habit.

DESCRIPTION OF THE NEW VARIETY

The following detailed descriptions set for the distinctive characteristics of 'PODARASNGA 3-30'. Measurements were taken from a 5-month-old plant, potted in a 3-gallon container and grown outdoors under irrigation. Color references are to The R.H.S. Colour Chart of The Royal Horticultural Society of London (R.H.S.) 2001, Fourth Edition.

Classification:

*Family.*—Scrophulariacace.

*Botanical.*—*Buddleia* x *hybrida* (*Buddleia davidii* x *B. crispa* x *B. alternifolia* x *B. lindleyana*).

*Designation.*—'PODARASNGA 3-30'.

Plant:

*Type and habit.*—Deciduous shrub with a vigorous growth habit; has a profuse number of flowers at each branch terminus; readily produces branches at each node; has horizontal branches with vertical secondary branches terminating in an inflorescence; very fastigiate habit.

*Form.*—Oval, horizontal and low to the ground.

*Height* (*at crown and measured from the top of the soil*).—140 cm.

*Width* (*horizontal plant diameter*).—150 to 200 cm.

*Time to produce a finished plant.*—To produce a 4-inch plant: 5 to 6 weeks from cuttings. To produce a 1-gallon pot: 8 to 10 weeks.

*Outdoor plant performance.*—Excellent in average soil structure with full sun; average fertility and water usage.

*Natural flowering season.*—At least 4 weeks before *B. davidii* and continuing up to a hard frost.

*Time to initiate and develop roots.*—7 to 10 days using 3,000 to 4,000 ppm IBA (indolebutyric acid) for tougher plant material or 2,000 ppm IBA for softer plant material.

*Root description and habit.*—Dense and fibrous; roots are RHS 20B.

*Propagation type.*—Softwood cuttings.

*Hardiness.*—Hardy to USDA Zone 6, possibly hardy in USDA Zone 5b; pruning is not recommended after August.

Lateral branches:

*General.*—Mature branches are 4-sided.

*Quantity per plant.*—About 19 horizontal primary branches and 73 vertical secondary branches terminating in inflorescence.

*Length.*—Primary branches range from about 43.0 cm to 46.0 cm; secondary vertical branches range from about 14.0 cm to 20.0 cm.

*Internode length.*—Primary branches range from 2.0 to 4.0 cm; secondary branches range from 3.0 cm to 5.0 cm.

*Diameter, for all branches.*—About 0.5 cm; from midpoint, about 0.25 cm.

*Color.*—Branches exposed to sunlight are RHS 181C; branches not exposed to sunlight are RHS 166D.

*Angle of branch attachment.*—About 180 degrees for primary branches and about 90 degrees for secondary branches which are pliable.

*Texture.*—Floccose.

*Strength.*—

*Anthocyanin.*—RHS N187A.

Leaves:

*Leaf arrangement and quantity.*—32 leaves per branch; opposite; about 10 pairs of leaves on the primary horizontal branches; about 6 pairs of leaves on the secondary vertical branches.

*Length.*—2 cm nearest flower panicle to 13 cm near base of plant.

*Width.*—0.75 cm nearest the flower panicle to 4.5 cm at the base of the plant.

*Shape and appearance.*—Lanceolate and rugose.

*Apex.*—Aristulate.

*Base.*—Shortly attenuate.

*Margin.*—Weakly denticulate; crenulate under magnification with denticulate tips.

*Texture.*—Upper surface: Pubescent and weakly rugose with many RHS 17A papillate glands. Lower surface: Strongly floccose; upon removal of floccose, RHS 17A papillate glands cover the lower surface.

*Color, immature.*—Upper surface: RHS 138A. Lower surface: RHS 195D.

*Color, mature.*—Upper surface: RHS 137A. Lower surface: RHS 195B.

*Venation pattern.*—Pinnate with RHS 17A papillate glands on the veins.

*Venation color.*—Upper surface: RHS 195C. Lower surface: RHS 195C.

*Petiole.*—Length: 0.7 cm to 0.8 cm. Diameter: 0.2 cm. Texture: Strongly floccose. Color: RHS 146B with RHS 17A papillate glands.

Inflorescence (panicle):

*Appearance.*—Panicles are elongated and conical in shape; terminal inflorescence is frequently three in number with the center inflorescence being longer than the two axillary inflorescences; panicle stem attachment on a primary stem is vertical and on a secondary stem, ranges from vertical to less than 30 degrees.

*Height.*—Of primary inflorescence/panicle: Between about 10.5 cm to 17.6 cm. Of two axillary inflorescence/panicles: Between about 5.5 cm to 12.5 cm.

*Width.*—Of primary inflorescence/panicle: Between about 3.0 cm and 4.1 cm. Of two axillary inflorescence/panicles: Between about 2.0 cm to 2.4 cm.

*Bud.*—General: Buds begin as a bud cluster and are RHS 145A with RHS N92A at the tip and as the buds mature, they become individualized and enlarge; the length of the bud cluster is 1.0 cm and the width of the bud cluster is 0.4 cm. Shape: Strongly conical. Texture: Strongly floccose. Length: 3.5 cm. Width: 1.0 cm. Color: RHS N92A.

*Flower.*—Type and habit: Single and salverform flowers arranged in compound terminal panicles which are elongated-conical in shape; flowers face upright and outward. Fragrance: Very fragrant. Lastingness of flowers on the plant: 7 to 10 days. Quantity of flowers per inflorescence (panicle): About 748. Depth: 1.0 cm. Diameter: 0.15 cm.

*Petals.*—Arrangement: Four or five petals arranged in a single whorl with the petals fused for form a tube. Shape: Rotund overall with jagged edges randomly varying between crenate and erose patterns edges. Apex: Salver-shaped. Base: Fused. Margin: Repand. Texture (both upper and lower surfaces): Floccose and glossy. Length: 0.4 cm. Width: 0.4 cm. Color, immature (both upper and lower surfaces): RHS N92B. Color, mature (both upper and lower surfaces): RHS N80A.

*Corolla tube.*—Length: 1.0 cm. Width: 0.15 cm. Color: Inner surface: RHS N163. Outer surface: RHS N80A. Between the throat and petal: RHS 158A. Texture: Inner surface: Hirsute; white hairs surround the interior of the tube and are angled outward. Outer surface: Floccose.

*Calyx.*—Arrangement and quantity per flower: Five sepals arranged in a single whorl and fused at the base. Sepals: Shape: Ligulate. Apex: Acute. Base: Fused. Margin: Entire. Length: 3.0 cm. Width: 0.05 cm. Texture: Upper surface: Floccose. Lower surface: Smooth. Color (both upper and lower surfaces): RHS 137B.

*Peduncle.*—Length: 0.5 cm to 2.5 cm. Diameter: 0.3 to 0.4 cm. Strength: Flexible; less than 40-degree bend. Color: RHS 166D. Texture: Floccose.

*Pedicel.*—Length: 0.05 cm. Diameter: 0.01 cm. Color: RHS 166D. Texture: Floccose.

Reproductive organs:

*Stamens.*—Quantity per flower: 5. Filament: General: Completely fused to corolla tube. Anther: Length: 0.1 cm. Color: RHS 4C. Pollen amount: Moderate.

*Pistil.*—Quantity per flower: 1. Length: 0.4 cm. Stigma: Shape and appearance: Spatulate-appearing in some instances with two barely distinguishable lobes; sometimes darkly pigmented at the very tip same color as corolla tube. Color: RHS 141C. Style: Length: 0.1 cm. Color: RHS N155A. Ovary: Shape and position: Globular and superior. Width: 0.1 cm. Color: RHS 141C with RHS 155B (White) floccose.

Seed:

*General.*—Seeds are enclosed in the ovary capsule; the seeds and the capsule are a dark black, but darker than any RHS color; no description of seed as seed has not been observed at maturity.

Disease and insect resistance: None observed.

COMPARISON WITH COMMERCIAL VARIETY

When 'PODARASNGA 3-30' is compared to the commercial variety 'Violet Cascade' (U.S. Plant Pat. No. 34,298), 'PODARASNGA 3-30' is 45.5 cm in height, while 'Violet Cascade' is 122 cm in height.

When 'PODARASNGA 3-30' is compared to the female parent, an un-named, unpatented proprietary *Buddleia* hybrid, 'PODARASNGA 3-30' has darker pigmentation of blooms and shorter stature than the female parent.

When 'PODARASNGA 3-30' is compared to the male parent, an un-named, unpatented proprietary *Buddleia* hybrid, 'PODARASNGA 3-30' has darker pigmented flowers and more dense branching structure than the male parent.

I claim:

1. A new and distinct cultivar of *Buddleia* Plant Named 'PodarasNGA 3-30' as described and illustrated herein.

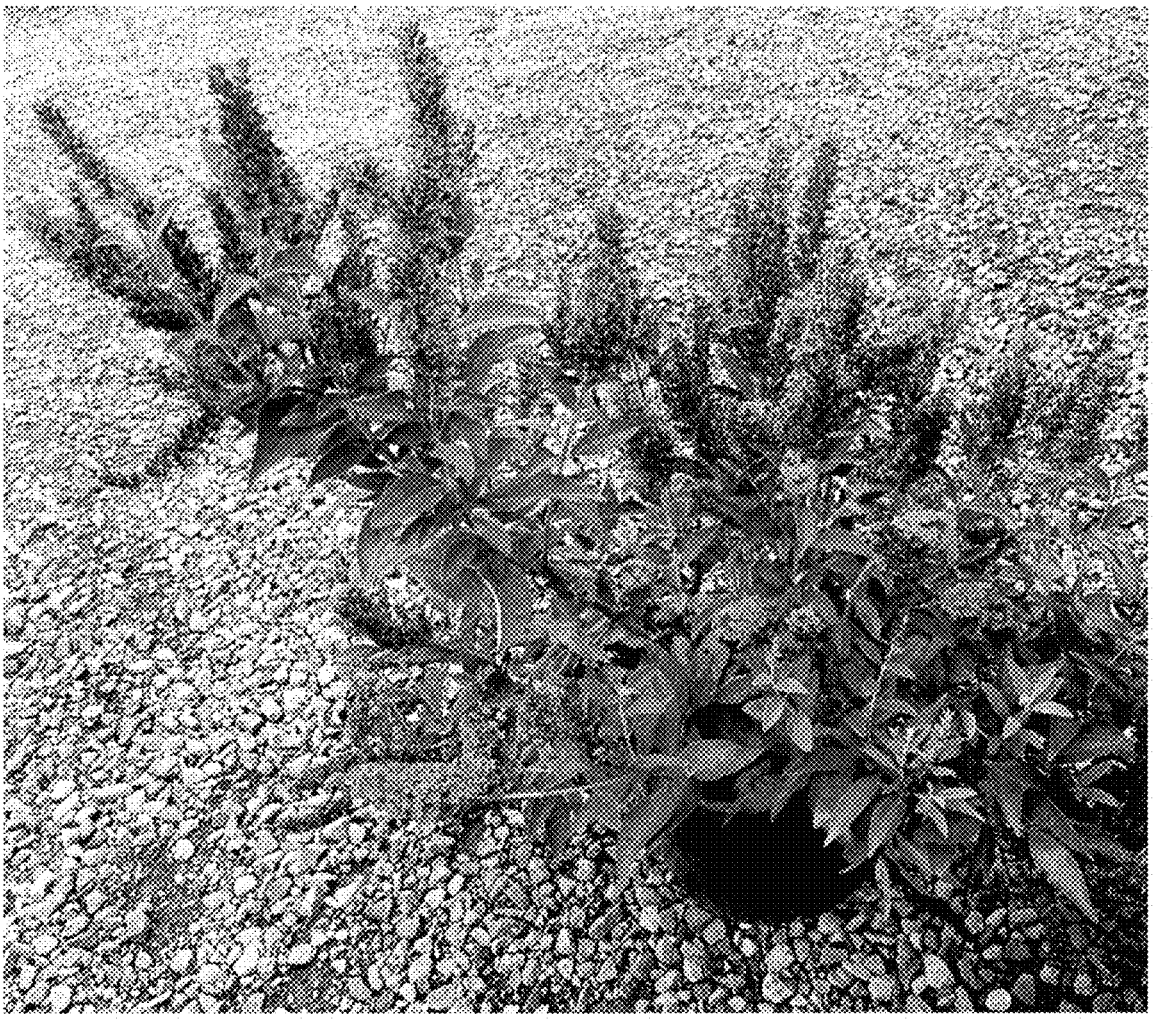

* * * * *